(12) United States Patent
Gutierrez et al.

(10) Patent No.: US 6,453,726 B1
(45) Date of Patent: Sep. 24, 2002

(54) GAS SENSOR WITH U-TYPE GASKET

(75) Inventors: Carlos A. Gutierrez, Grand Blanc; Charles Scott Nelson, Clio; Kathryn Mary McCauley, Durand, all of MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/731,417

(22) Filed: Dec. 6, 2000

(51) Int. Cl.[7] .............................. G01N 27/409
(52) U.S. Cl. ................. 73/31.05; 73/23.31; 204/424
(58) Field of Search ................. 73/23.2, 23.31, 73/31.05, 31.06; 204/424, 426, 428

(56) References Cited

U.S. PATENT DOCUMENTS

| | | | | |
|---|---|---|---|---|
| 5,031,445 A | * | 7/1991 | Kato et al. ................. | 204/424 |
| 5,329,806 A | * | 7/1994 | McClanahan et al. ...... | 436/137 |
| 6,063,249 A | * | 5/2000 | Duce et al. ................. | 204/424 |
| 6,082,175 A | * | 7/2000 | Yoshikawa et al. ......... | 204/426 |
| 6,322,681 B1 | * | 11/2001 | Weyl .......................... | 204/424 |

* cited by examiner

Primary Examiner—Hezron Williams
Assistant Examiner—Michael Cygan
(74) Attorney, Agent, or Firm—Vincent A. Cichosz

(57) ABSTRACT

The gas sensor comprises a sensor element; a shell disposed around at least a portion of the sensor element, the shell having a projecting edge from a first end, wherein a portion of the projecting edge is bent toward the sensing element; an upper shield disposed around at least a portion of the sensor element, the upper shield having a terminal end; a gasket disposed between the projecting edge and the terminal end, wherein the gasket is a U-type gasket; and a lower shield affixed to a second end of the shell.

32 Claims, 3 Drawing Sheets

GAS SENSOR WITH U-TYPE GASKET

TECHNICAL FIELD

The present invention relates to gas sensors. More particularly, the present invention relates to a gas sensor with a crimp design.

BACKGROUND OF THE INVENTION

Exhaust gas sensors are used in a variety of applications that require qualitative and quantitative analysis of gases. For example, exhaust gas sensors have been used for many years in automotive vehicles to sense the presence of oxygen in exhaust gases, for example, to sense when an exhaust gas content switches from rich to lean or lean to rich. In automotive applications, the direct relationship between oxygen concentration in the exhaust gas and the air-to-fuel ratios of the fuel mixture supplied to the engine allows the exhaust sensor to provide oxygen concentration measurements for determination of optimum combustion conditions, maximization of fuel economy, and the management of exhaust emissions.

A conventional stoichiometric sensor typically consists of an ionically conductive solid electrolyte material, a porous electrode on the sensor's exterior exposed to the exhaust gases with a porous protective overcoat, and a porous electrode on the sensor's interior surface exposed to a known gas partial pressure. Sensors typically used in automotive applications use a yttria stabilized zirconia based electrochemical galvanic cell with porous platinum electrodes, operating in potentiometric mode, to detect the relative amounts of oxygen present in an automobile engine's exhaust. When opposite surfaces of this galvanic cell are exposed to different oxygen partial pressures, an electromotive force (emf) is developed between the electrodes on the opposite surfaces of the electrolyte wall, according to the Nernst equation:

$$E = \left(\frac{-RT}{4F}\right) \ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas Due to the large difference in oxygen partial pressures between fuel-rich and fuel-lean exhaust conditions, the electromotive force changes sharply at the stoichiometric point, giving rise to the characteristic switching behavior of these sensors. Consequently, these potentiometric sensors indicate qualitatively whether the engine is operating fuel-rich or fuel-lean, without quantifying the actual air to fuel ratio of the exhaust mixture.

One known type of exhaust sensor includes a flat plate sensor formed of various layers of ceramic and electrolyte materials laminated and sintered together with electrical circuit and sensor traces placed between the layers in a known manner. The flat plate sensing element can be both difficult and expensive to package within the body of the exhaust sensor since it generally has one dimension that is very thin and is usually made of brittle materials. Consequently, great care and time consuming effort must be taken to prevent the flat plate sensing element from being damaged by exhaust, heat, impact, vibration, the environment, etc. This is particularly problematic since most materials conventionally used as sensing element supports, for example, glass and ceramics, typically have a high modulus of elasticity and cannot withstand much bending. Hence, great care and expense is expended in preventing manufacturing failures.

Accordingly, there remains a need in the art for a low cost, temperature resistant sensor package.

SUMMARY OF THE INVENTION

The drawbacks and disadvantages of the prior art are overcome by the gas sensor and method for making the same. The gas sensor comprises a sensor element; a shell disposed around at least a portion of the sensor element, the shell having a projecting edge from a first end, wherein a portion of the projecting edge is bent toward the sensing element; an upper shield disposed around at least a portion of the sensor element, the upper shield having a terminal end; a gasket disposed between the projecting edge and the terminal end, wherein the gasket is a U-type gasket; and a lower shield affixed to a second end of the shell.

The method of forming the gas sensor comprises providing a shell having a projecting edge from a first end and a segment, wherein the segment is substantially perpendicular to the projecting edge; providing an upper shield having a terminal end with a first side and a second side, wherein the first side of the terminal end is positioned adjacent to the segment; positioning a gasket on the second side of the terminal end, wherein the gasket is a U-type gasket; forming a bent portion of the shell by bending at least a portion of the projecting edge of the shell about the gasket and the terminal end; affixing a lower shield to a second end of the shell; and extending a sensor element through the upper shield, through the shell into the lower shield.

The above described and other features and advantages of the present invention will be appreciated and understood by those skilled in the art from the following detailed description, drawings, and appended claims.

BRIEF DESCRIPTION OF THE DRAWINGS

The gas sensor will now be described by way of example with reference to the following Figures, which are meant to be exemplary, not limiting.

DESCRIPTION OF THE PREFERRED EMBODIMENT

Sensor shields and shells are typically crimped to adjoin the sections to form completed exhaust sensors. An exhaust sensor disclosed herein advantageously utilizes a crimp design. Typically, exhaust sensors are constructed to endure an exhaust gas environment while protecting the sensor components. Because of the sensor component fragility, the manufacturing process can be difficult and expensive. To preserve the components, a shield and shell are formed around the sensing element to form a unitary sensor. To maintain a unitary structure, shields and shell are commonly adjoined together by, for example, crimping, welding, and/or adhesives.

Figure 1:
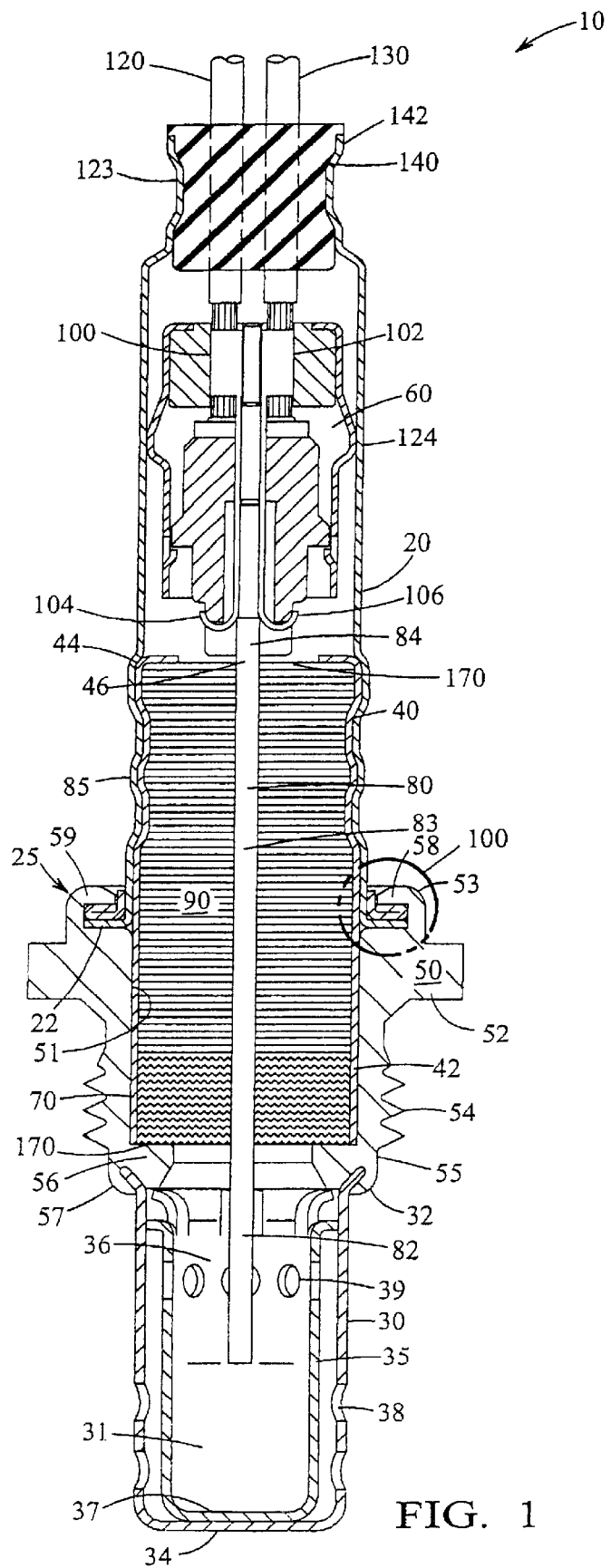
FIG. 1 is a cross-sectional side view of one embodiment of an exhaust sensor utilizing a crimp.

Referring to FIG. 1, an exemplary exhaust sensor 10 is shown employing a crimp 58 of upper shield 20 to shell 50 with gasket 25 disposed in between upper shield 20 and shell 50 in accordance with the present invention. Exhaust sensor 10 includes a housing structure generally formed of an upper shield 20 disposed adjacent to a first end of shell 50. A lower shield 30 is disposed adjacent to a second end of shell 50. Inner shield 40 is optionally disposed within a portion of both upper shield 20 and shell 50. A terminal connector 60 and a portion of a sensing element 80 are disposed within upper shield 20. Sensing element 80 is a pumped-air reference exhaust sensing element of a known type with any conventional geometry, such as a generally flat, elongated, rectangular shape. At a first end 82 thereof, sensing element 80 includes an exhaust constituent-responsive structure fabricated into sensing element 80 in a known manner, preferably along with a heater (not shown) of a known type.

Exhaust sensor 10 advantageously utilizes crimp 58 to adhere upper shield 20 to shell 50. Crimp 58 is comprised of first end 53 of shell 50 being disposed proximate to terminal end 22 of upper shield 20. First end 53 of shell 50 is formed as a projecting edge or lip of material spaced apart from inner shield 40 and shell inner edge 51 to form segment 59. Segment 59 is shown as a flat length, disposed substantially perpendicular to the length of upper shield 20, but can also comprise any angle. Terminal end 22 of the upper shield 20 is formed to extend away from the main axis of sensing element 10 (i.e., at an angle from the sensing element 80), with a substantially perpendicular extension 67 of the terminal end 22 preferred (see FIGS. 5 and 6), and a length sufficient to enable engagement by crimp 58. This terminal end 22 is then placed juxtaposition to segment 59 to rest thereupon. Segment 59 need be of sufficient length so that when crimp 58 is formed, it will engage the terminal end 22 and hold it securely within the wrapped lip of first end 53.

Figure 2:
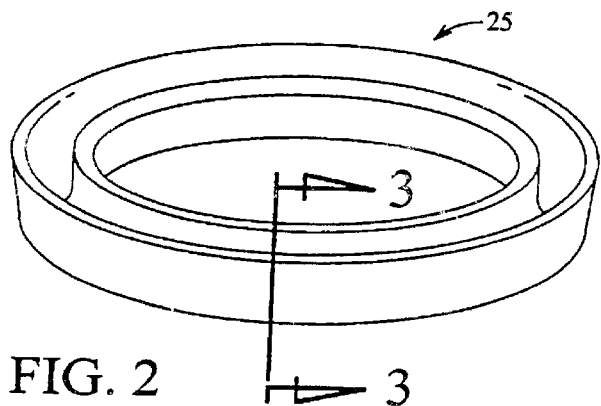
FIG. 2 is an isometric view of one embodiment of a U-type gasket.
Figure 3:
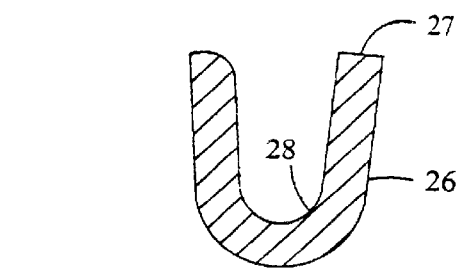
FIG. 3 is a cross-sectional view of one embodiment of a U-type gasket taken along lines 3—3 of FIG. 2.

Disposed between crimp 58 and extension 67, is a gasket 25. FIGS. 2 and 3 illustrate gasket 25, a U-type gasket with a cross-sectional shape of a 'U'. Gasket 25 is disposed between the wrapped lip end of first end 53 and terminal end 22. Gasket 25 can be formed from any suitable material compatible with an exhaust environment and capable of providing a gas tight seal. The gasket material is preferably a balance of various mechanical properties including yield strength, ultimate tensile strength, and elongation. For example, the gasket material preferably comprises a yield strength of about 300 MPa or greater, an ultimate tensile strength of about 500 MPa or greater, and an elongation of about 10% or greater; with a yield strength of about 600 MPa or greater, an ultimate tensile strength of about 800 MPa or greater, and an elongation of about 10% to about 35% preferred; and a yield strength of about 900 MPa or greater, an ultimate tensile strength of about 1,000 MPa or greater, and an elongation of about 10% to about 27% especially preferred. Some possible materials include ferrous materials, such as stainless steels and the like, e.g., high chrome stainless steel, high nickel stainless steel, and others, as well as combinations comprising at least one of the foregoing materials.

Gasket 25 can be formed by traditional machining or forming techniques. Referring to FIG. 3, the finish of outer surface 26 is preferably smooth (i.e., free of visible flaws, machining marks, and burrs) to enable a fluid tight seal. The U-type gasket 25 can comprise numerous geometries, with an overall "U" shape. For example, the bottom 27, can be rounded, squared, multi-sided, or any combination thereof; the sides can be of equal or different lengths, and the top edge 27 can be straight or rounded. Inner radius 28 is determined by the size of the gasket required and machining/forming capabilities. Optionally, once gasket 25 is formed, it can be annealed before installation.

Figure 5:
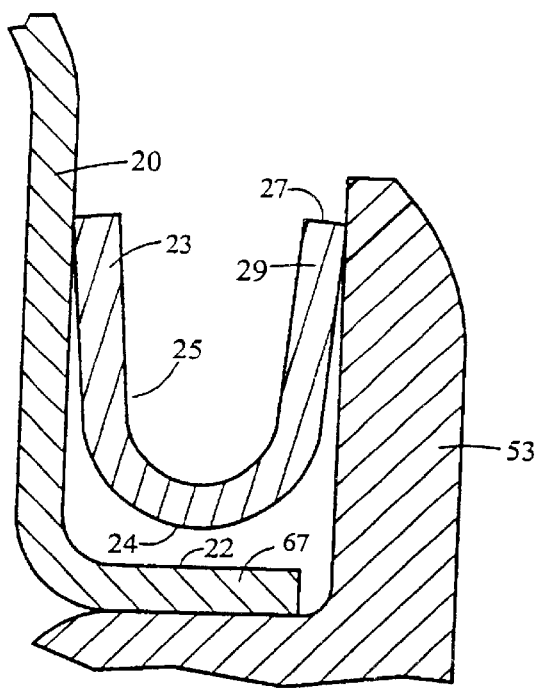
FIGS. 5 and 6 are partial, cross-sectional, exploded views of the seal area 100 from FIG. 1.
Figure 6:
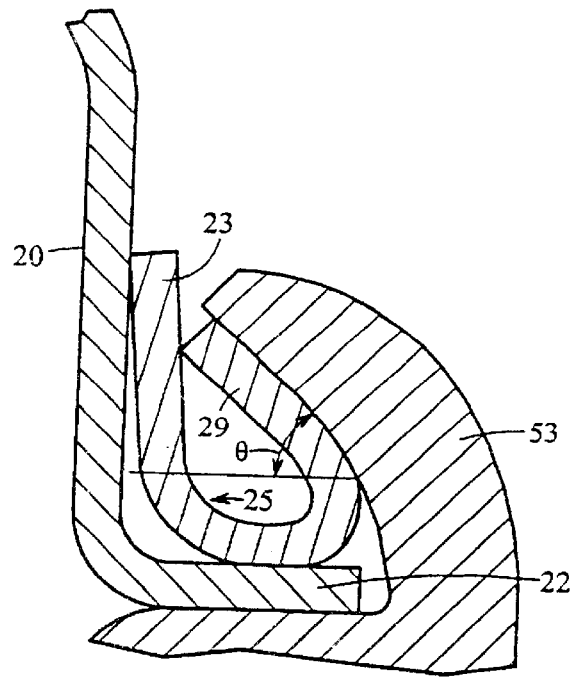

Referring to FIGS. 5 and 6, the gasket 25 can be disposed between the upper shield 20 and the first end 53 such that: (i) the side 23 physically contacts the upper shield 20 and the side 29 physically contacts the first end 53; (ii) the side 23 physically contacts the upper shield 20, while the side 29 is disposed in a spaced relation to the first end 53; or (iii) the side 23 is disposed in a spaced relation to the upper shield 20, while the side 29 physically contacts the first end 53. Consequently, upon crimping of first end 53, the side 29 will be bent toward side 23 and optionally toward base 24. The final orientation of side 29 will be dependent upon the desired final crimp angle θ. Angle θ should be sufficient to create a fluid tight seal which inhibits fluid access to the sensing element through the crimp. Generally, the angle θ can be from 0° to about 75° (depending upon the gasket size), with angles of 0° to about 45° typically preferred.

Figure 4:
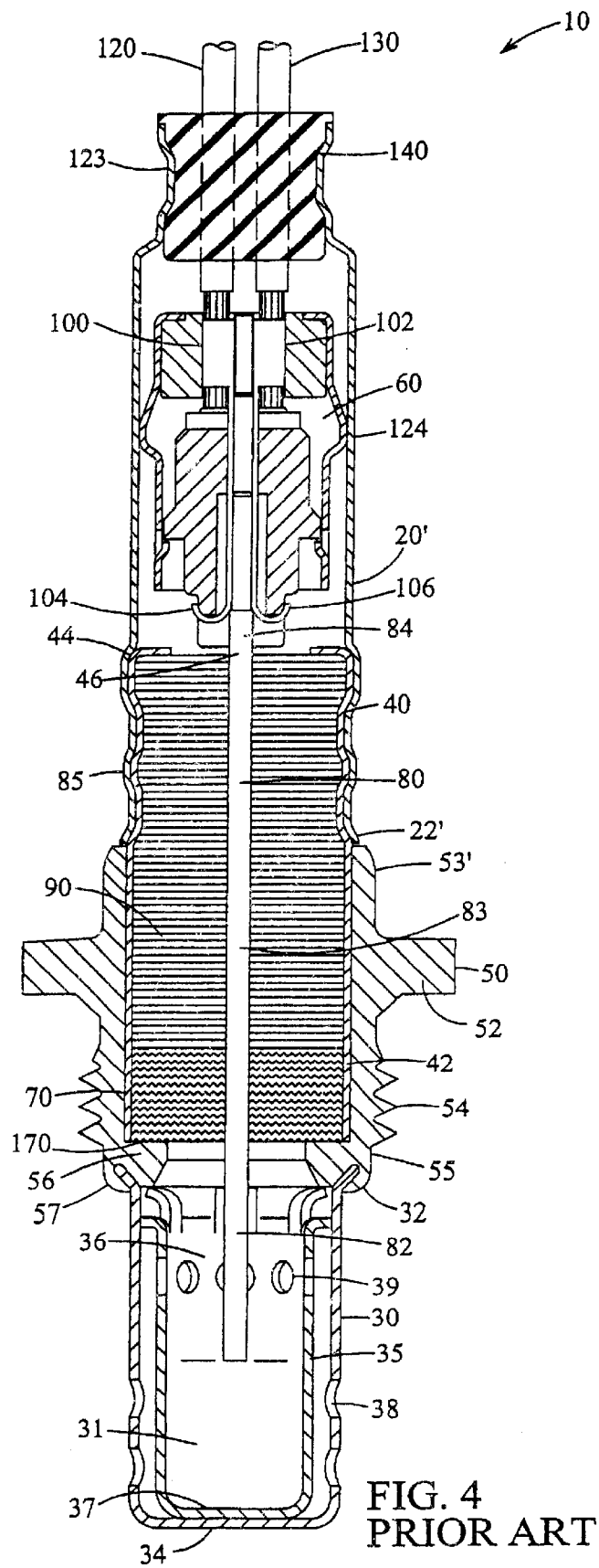
FIG. 4 is a prior art cross-sectional side view of an exhaust sensor utilizing a standard crimp.

This crimping arrangement negates the need for a high pressure crimp of upper shield 20 to inner shield 40 and of shell 50 to inner shield 40 and creates only one sealing surface. For example, a prior art high pressure crimp required a pressure directed inward toward the sensor element of about 2,000 pounds per square inch (p.s.i.) whereas crimping shell end 53 over upper shell extension 67 uses a pressure applied, at least partially, in a parallel direction to the sensor element, sufficient to dispose first end 53 inward, e.g., a pressure of about 10,000 p.s.i. to about 30,000 p.s.i., and more preferably about 10,000 to about 20,000 p.s.i. Basically, at no time during the formation of this crimp is a pressure required to deform inner shield 40. Consequently, even during crimping, it is not necessary to expose the sensing element to elevated pressure as required by the prior art. As to the one sealing surface, this is formed between upper shield 20, shell 50, and inner shell 40. Whereas in the prior art, two sealing surfaces were created where shell 50 met inner shield 40 and where upper shield 20 met shell 50 (See FIG. 4).

Sensor 10 can be formed by known manufacturing techniques with the exception that upper shield 20 and components therein are mated to shell 50 and components therein so that terminal end 22 is positioned juxtaposition to segment 59. Thereafter, gasket 25 is disposed on terminal end 22 and force is applied so that the wrapped lip of first end 53 is formed. This is particularly advantageous because the force used to form the wrapped lip is not transferred inward to the sensor element 80. Instead, the force is substantially only directed at first end 53, and is substantially directed in an approximately parallel or angled direction to the length of sensor element 80. As the force is applied to first end of shell 53, gasket 25 will deform, as illustrated in FIG. 1, resulting in a sealed surface between terminal end 22 and shell 50 along segment 59. Referring to prior art FIG. 4, first end 53' rests flatly against inner shield 40 to meet or about meet terminal end 22' of upper shield 20'. Hence, a portion of inner shield 40 may be directly exposed to the exterior environment. The prior art sensor first end 53' does not form a projecting edge or lip of material to engage terminal end 22'. Therefore, the prior art assembly utilizes inward pressure crimps 85 to attach and retain upper shield 20 to inner shield 40 and to attach inner shield 40 to shell 50. The use of high pressure inward crimps by the prior art endanger the fragile sensor element 80 and thus increases the chance for failure and scrap due to the higher stresses placed upon the sensor.

Again referring to FIG. 1, as to the remaining structure of sensor 10, shell 50 includes a body portion 52 and a threaded portion 54 at a second end 55. Body portion 52 is preferably shaped to accommodate a wrench or other tool for tightening threaded portion 54 into a mount for an exhaust pipe or other component of an exhaust flow system enabling a sensor chamber 31 located within lower shield 30 to be located within a flow of exhaust gasses to be measured. Additionally, shell 50 is securely disposed around inner shield 40 and holds inner shield 40 via a compressive force engagement. Formed at second end 55 of shell 50 is a shoulder 56 for contacting first end 42 of inner shield 40, whereby inner shield 40 can rest against shoulder 56 when shell 50 is secured to inner shield 40 during assembly.

Adjoined and partially encased by a bottom portion of upper shield 20, inner shield 40 has a first end 42 and a preferably partially closed second end 44 opposite first end 42. A centrally located annular opening 46 is provided at second end 44 and is sized to allow insertion of element second end 84 of sensing element 80 therethrough. Disposed within at least a portion of inner shield 40 is a central portion 83 of sensing element 80 and a high temperature material 90. Optionally, a pair of thermal insulating members (not shown) may be disposed against the sensing element 80 for additional support as is known in the art.

High temperature material 90, which can extend through part of all of inner shield 40, is concentrically disposed around sensing element 80. As used herein, the term "high temperature material" refers to materials that are designed for use in a spark ignition engine environment, where temperatures range up to about 1,000° C. Such materials include ceramic fibrous materials, and/or metal mesh, among others. When a ceramic fibrous material is used, the orientation and size of the ceramic fibers are not critical. High temperature material 90 may be installed in either a preform or fibrous blanket type state around at least a portion of sensing element 80 as is known in the relevant arts.

Exhaust erosion of high temperature material 90 and terminal connector 60 may be prevented in a particularly advantageous embodiment, which further comprises a disk supporting device and/or a metal mesh support, distinct from the high temperature material. These supports are capable, individually or in tandem, of providing secure support of the sensing element in the weak axis direction, and of preventing excessive exhaust erosion of sensitive sensor components.

A disk element support 170 is positioned between partially closed second end 44 of inner shield 40 and mat 90, concentrically around sensing element 80. Disk element support 170 may also (or alternatively) be positioned between shoulder 56 of shell 50 and mat support 90. Also, an aperture is provided therein, through which the sensing element 80 may be inserted.

Disk element support 170 is made of a material compatible with the environmental conditions of the sensor. Specifically, the disk element support 170 is capable of maintaining structural integrity in a high temperature environment (up to about 1,000° C.). Exemplary materials include metal, ceramic, talc, composites, combinations combining at least one of the foregoing materials and other materials compatible with the sensor environment.

A mesh 70 can optionally be located between high temperature material 90 and sensing chamber 31 or high temperature material 90 and disk element support 170. The mesh can be made from fine wire, impregnated with a filler material, e.g. clay, talc, or the like, to fill the space between the mesh fibers, and compressed into desired form. Wire material may be made of any metal, such as ferrous materials, however, stainless steels with high nickel or chrome content are preferred due to their corrosion resistant properties. Particularly preferred metals include 310, 309, and 316 stainless steels. Suitable thickness for fine wire material used as a mesh element support is about 0.2 to about 1.2 millimeters, with about 0.4 to about 0.6 millimeters being preferred. Preferred wire densities are about 20% to about 50% of the solid density, with the filler material making up the difference, giving a solid density of about 50% to about 70%.

At a second end 84 of sensing element 80, lower ends 104 and 106 of terminals 100 and 102, respectively, contact external pads (not shown) on end 84 to provide electrical connection between terminals 100 and 102 and sensing element 80. Ends 104 and 106 of terminals 100 and 102, respectively, are maintained against second end 84 of sensing element 80 by a compressive force applied by disposing second end 84 of sensing element 80 between lower ends 104 and 106. Preferably, terminals 100 and 102 comprise spring terminals, as is known in the art, such that the compressive force generated by disposing second end 84 between spring terminals 100 and 102 securely maintains end 84 in electrical contact therewith. While spring terminals are disclosed herein, other known terminals that allow an electrical connection may be used.

To allow an electrical connection of sensing element 80, a terminal connecter 60 can be used. The use of terminal connector 60 is known in the art and a suitable terminal connector 60 is also known in the art as an edge card connector, a clam shell connector, or the like. Terminal connector 60 typically includes a plurality of electrical terminals with each having a corresponding electrical wire connected thereto.

For the purpose of illustration only, sensor 10 is shown having a pair of electrical terminals 100 and 102, which are adapted to be connected to electrical wires 120 and 130 in a known manner. Electrical wires 120 and 130 pass through cable seal 140, which generally comprises an elastomeric material suitable for use in a high temperature environments (e.g., spark ignition engine with temperatures up to about 1,000° C.), without failing. Cable seal 140 is maintained in place by upper shield 20, which has an upper end 123 forming a seal around a shoulder 142 of cable seal 140, wherein upper shield 20 can be crimped in place around cable seal 140 to further secure the same. A central portion 124 of upper shield 20 is disposed around terminal connector 60 while terminal end 22 of upper shield 20 forms an opening preferably tightly fit around inner shield second end 44 when sensor 10 is assembled. Generally, the upper shield 20 has a geometry complimentary with the inner shield 20 geometry, such as cylindrical, elliptical, multi-sided, or the like.

In a generally preferred configuration, lower shield 30 is securely coupled to shell 50 by engaging flared open end 32 of lower shield 30 with annular recess 57. Shell 50 is itself securely coupled to upper shield 20 and thereby to optional inner shield 40 which is further secured by shoulder 56. Consequently, sensing element 80 is disposed through inner shield 40 with a first end 82 extending within sensing chamber 31. Lower shield 30 defines sensing chamber 31 and disposed within lower shield 30 can be an internal shield 35, which has an open end 36 for receiving sensing element 80 and an optional closed end 37 adjacent and parallel to closed end 34 of lower shield 30. Lower shield 30 and internal shield 35 incorporate a plurality of apertures 38, 39 on lower shield 30 and on internal shield 35, respectively, for allowing passage of exhaust gas in and out of sensing chamber 31 so that the gasses may be sensed by receptive first end 82 of sensing element 80.

As to the sensor's other materials, exemplary materials for the shields 20, 30, 40, and 35 and for the shell 50 include ferrous materials such as stainless steel, e.g., high chrome, high nickel stainless steel, and mixture comprising at least one of the foregoing materials, and the like, with all steels chosen for high temperature endurance, high-strength and corrosion resistance. Terminal connector 60 may be formed of thermoplastic and/or thermoset materials (e.g., plastic) or ceramic durable in the high temperature environments to which exhaust sensor 10 is exposed.

This sensor employs a seal design which reduces stress on the sensing element, reduces potential leak paths into the sensor, and simplifies overall sensor production. Basically a more robust and simplified product can be produced that is less likely to leak from the adjoining of upper shield 20 to shell 50 since the crimp forms only a single sealing surface between upper shield 20 and shell 50 through the use of gasket 25, reducing potential leak points.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A gas sensor, comprising:
   a sensor element;
   a shell disposed around at least a portion of the sensor element, the shell having a projecting edge spaced apart from an inner surface and protruding from a first end, wherein a portion of the projecting edge is bent toward the sensing element to form a crimp;
   an upper shield disposed around at least a portion of the sensor element, the upper shield having a terminal end engaged within the crimp;
   a u-shaped gasket having a u-shaped cross-section formed separately from said shell and said upper shield, said u-shaped gasket being disposed between the projecting edge and the terminal end; and a lower shield disposed around a portion of the sensing element and affixed to a second end of the shell.

2. The gas sensor of claim 1, further comprising an inner shield disposed around the sensor element and positioned within an upper shield second end and the shell.

3. The gas sensor of claim 1, wherein the gasket comprises a ferrous material.

4. The gas sensor of claim 3, wherein the gasket comprises a material selected from the group consisting of stainless steel, high chrome stainless steel, high nickel stainless steel, and combinations comprising at least one of the foregoing materials.

5. The gas sensor of claim 4, wherein the gasket is annealed before installation.

6. The gas sensor of claim 1, wherein the gasket comprises a yield strength of about 300 MPa or greater.

7. The gas sensor of claim 6, wherein the gasket comprises a yield strength of about 600 MPa or greater.

8. The gas sensor of claim 7, wherein the gasket comprises a yield strength of about 900 MPa or greater.

9. The gas sensor of claim 1, wherein the gasket comprises an ultimate tensile strength of about 500 MPa or greater.

10. The gas sensor of claim 9, wherein the gasket comprises an ultimate tensile strength of about 800 MPa or greater.

11. The gas sensor of claim 10, wherein the gasket comprises an ultimate tensile strength of about 1,200 MPa or greater.

12. The gas sensor of claim 1, wherein the gasket comprises an elongation of about 10% or greater.

13. The gas sensor of claim 12, wherein the gasket comprises an elongation of about 10% to about 35%.

14. The gas sensor of claim 13, wherein the gasket comprises an elongation of about 10% to about 27%.

15. A method of forming a gas sensor, comprising:
    providing a shell having a projecting edge from a first end and a segment, wherein the segment is substantially perpendicular to the projecting edge;
    providing an upper shield having a terminal end with a first side and a second side, wherein the first side of the terminal end is positioned adjacent to the segment;
    positioning a gasket on the second side of the terminal end, wherein the gasket is a U-type gasket having a u-shaped cross-section and is formed separately from said shell and said upper shield;
    forming a bent portion of the shell by bending at least a portion of the projecting edge of the shell about the gasket and the terminal end;
    affixing a lower shield to a second end of the shell; and extending a sensor element through the upper shield, through the shell into the lower shield.

16. The method of forming gas sensor of claim 15, further comprising positioning an inner shield within the upper shield and the shell.

17. The method of forming a gas sensor of claim 15, wherein the gasket comprises a ferrous material.

18. The method of forming a gas sensor of claim 17, wherein the gasket comprises a material selected from the group consisting of stainless steel, high chrome stainless steel, high nickel stainless steel, and combinations comprising at least one of the foregoing materials.

19. The method of forming a gas sensor of claim 18, wherein the gasket is annealed before the positioning of the gasket on the terminal end portion of the upper shield second end.

20. The method of forming a gas sensor of claim 15, wherein the gasket comprises a yield strength of about 300 MPa or greater.

21. The method of forming a gas sensor of claim 20, wherein the gasket comprises a yield strength of about 600 MPa or greater.

22. The method of forming a gas sensor of claim 20, wherein the gasket comprises a yield strength of about 900 MPa or greater.

23. The method of forming a gas sensor of claim 15, wherein the gasket comprises an ultimate tensile strength of about 500 MPa or greater.

24. The method of forming a gas sensor of claim 23, wherein the gasket comprises an ultimate tensile strength of about 800 MPa or greater.

25. The method of forming a gas sensor of claim 24, wherein the gasket comprises an ultimate tensile strength of about 1,200 MPa or greater.

26. The method of forming a gas sensor of claim 15, wherein the gasket comprises an elongation of about 10% or greater.

27. The method of forming a gas sensor of claim 26, wherein the gasket comprises an elongation of about 10% to about 35%.

28. The method of forming a gas sensor of claim 27, wherein the gasket comprises an elongation of about 10% to about 27%.

29. The method of forming a gas sensor of claim 15, wherein the gasket has a smooth surface finish.

30. The method of forming a gas sensor of claim 15, wherein the forming of the bent portion comprises applying pressure upon the projecting edge of the shell in a downward direction, parallel to the sensor element.

31. The method of forming a gas sensor of claim 30, wherein the pressure applied is about 10,000 p.s.i. to about 30,000 p.s.i.

32. The method of forming a gas sensor of claim 31, wherein the pressure applied is about 10,000 p.s.i. to about 20,000 p.s.i.

* * * * *